United States Patent
Castrantas et al.

(10) Patent No.: US 6,365,099 B1
(45) Date of Patent: Apr. 2, 2002

(54) IN SITU GAS SCRUBBING METHOD AND SYSTEM FOR ODOR AND CORROSION CONTROL IN WASTEWATER COLLECTION SYSTEMS

(75) Inventors: Harry M. Castrantas, Newtown, PA (US); Scott W. Duggan, Laguna Niguel, CA (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/190,532

(22) Filed: Nov. 12, 1998

(51) Int. Cl.$^7$ .............................. A61L 9/14; C01B 17/16
(52) U.S. Cl. .............................. 422/5; 422/123; 95/235; 96/243; 423/232; 423/243.01; 423/243.06; 423/243.08
(58) Field of Search ................................ 422/4, 5, 123, 422/306; 95/149, 235; 96/243; 423/220, 242.1, 243.01, 243.08, 243.06, 232

(56) References Cited

U.S. PATENT DOCUMENTS

| | | | |
|---|---|---|---|
| 3,911,080 A | 10/1975 | Mehl et al. | 423/210 |
| 3,969,479 A | 7/1976 | Lonnes et al. | 423/210 |
| 4,125,589 A | 11/1978 | DeVries | 423/245 |
| 4,172,880 A | 10/1979 | Tzavos | 423/210 |
| 4,225,566 A | 9/1980 | DeVries | 423/210 |
| 4,238,461 A | 12/1980 | Devries | 423/210 |
| 4,462,968 A | 7/1984 | Tazuma et al. | 423/224 |
| 4,574,076 A | 3/1986 | Castrantas | 423/224 |
| 4,844,874 A | 7/1989 | DeVries | 423/210 |
| 5,011,520 A | 4/1991 | Carr et al. | 55/228 |
| 5,417,920 A | 5/1995 | Yung | 422/5 |
| 5,738,834 A | 4/1998 | Deberry | 422/177 |
| 5,989,497 A | * 11/1999 | Labonte, Jr. | 422/4 X |
| 6,132,678 A | * 10/2000 | Heller et al. | 422/5 X |

OTHER PUBLICATIONS

"Scrubbing Hydrogen Sulfide with Hydrogen Peroxide", Pollution Control Release No. 8, FMC Corporation.
"Sulfur Compound Oxidation with Hydrogen Peroxide", Pollution Control Release No. 9, FMC Corporation.
"The Use of Hydrogen Peroxide for the Oxidation of Sulfur Chemical Wastes", Pollution Control Release No. 81, presented at the 7$^{th}$ Middle Atlantic Industrial Waste Conference, Drexel University, Philadelphia, PA, Nov. 13, 1974.

* cited by examiner

*Primary Examiner*—Elizabeth McKane
(74) *Attorney, Agent, or Firm*—Michael E. Martin; Patrick C. Baker

(57) ABSTRACT

A process and system for reducing the concentration of odorous contaminants, primarily hydrogen sulfide, in the vapor spaces of sewage handling and treatment systems, primarily the vapor spaces of sewage trunk lines, by injecting a fine spray, mist or fog of a dilute solution of hydrogen peroxide and a base selected from a group consisting of sodium hydroxide, potassium hydroxide, ammonium hydroxide and sodium carbonate to mix intimately with the vapor flow. The peroxide and base solutions may be premixed and diluted with water and injected through atomizing nozzles utilizing compressed air as an atomizing fluid. The system may also provide for separate storage of the peroxide and base solutions, mixing of the peroxide and base solutions with dilution water with in-line mixing devices and direct injection with or without compressed air atomization into the vapor space. Sewage trunk lines, in particular, are treated at a substantial distance upstream of the sewage treatment facility to allow for adequate reaction time to reduce the concentration of the contaminant and reduce loading and corrosion on sewage treatment and foul air handling and scrubbing equipment.

12 Claims, 3 Drawing Sheets

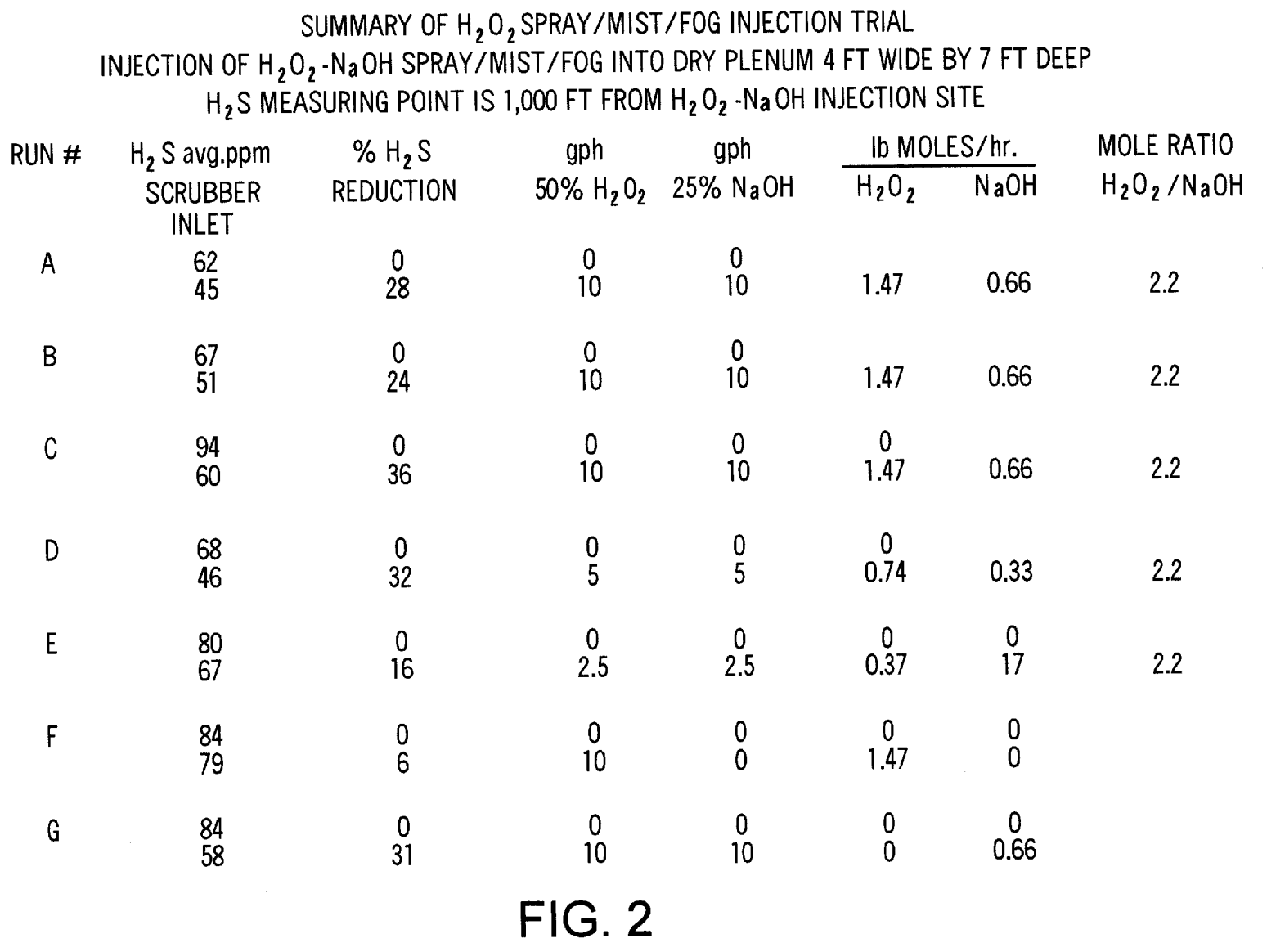

SUMMARY OF $H_2O_2$ SPRAY/MIST/FOG INJECTION TRIAL
INJEC

GRAVITY SEWER FOGGING TRIAL

| RUN NUMBER | FEED RATES gph 50% H$_2$O$_2$ | FEED RATES gph 25% NaOH | lb. MOLES/hr H$_2$O$_2$ | lb. MOLES/hr NaOH | MOLE RATIO H$_2$O$_2$/NaOH | TIME SEC | TIME SEC | ppm H$_2$S BEFORE TREATMENT | ppm H$_2$S AFTER TREATMENT | % H$_2$S REMOVAL |
|---|---|---|---|---|---|---|---|---|---|---|
| 1A | 0 | 0 | 0.00 | 0.00 | 0.0 | 850 | 0 | 70 | 70 | 0% |
| 1B | 0 | 0 | 0.00 | 0.00 | 0.0 | 1020 | 170 | 105 | 105 | 0% |
| 1C | 0 | 0 | 0.00 | 0.00 | 0.0 | 1230 | 380 | 170 | 170 | 0% |
| 1D | 0 | 0 | 0.00 | 0.00 | 0.0 | 1530 | 680 | 175 | 175 | 0% |
| 2A WATER SPRAY | 0 | 0 | 0.00 | 0.00 | 0.0 | 835 | 0 | 65 | 60 | 8% |
| 3A | 0 | 5 | 0.00 | 0.33 | 0.0 | 820 | 0 | 55 | 26 | 53% |
| 4A | 0 | 10 | 0.00 | 0.66 | 0.0 | 1510 | 300 | 175 | 80 | 54% |
| 5A | 0 | 0 | 0.00 | 0.00 | 0.0 | 920 | 0 | 70 | 60 | 14% |
| 6A | 5 | 5 | 0.74 | 0.33 | 2.2 | 1130 | 385 | 155 | 65 | 58% |
| 6B | 5 | 5 | 0.74 | 0.33 | 2.2 | 1330 | 585 | 170 | 73 | 57% |
| 7A | 5 | 5 | 0.74 | 0.33 | 2.2 | 745 | 0 | 45 | 15 | 67% |
| 7B | 5 | 5 | 0.74 | 0.33 | 2.2 | 905 | 160 | 70 | 24 | 66% |
| 8A | 10 | 10 | 1.47 | 0.66 | 2.2 | 1420 | 20 | 170 | 58 | 66% |
| 9A | 5 | 10 | 0.74 | 0.66 | 1.1 | 1155 | 0 | 160 | 51 | 68% |
| 9B | 5 | 10 | 0.74 | 0.66 | 1.1 | 1435 | 280 | 170 | 60 | 65% |
| 10A | 10 | 5 | 1.47 | 0.33 | 4.5 | 1400 | 0 | 170 | 73 | 57% |
| 11A | 2.5 | 2.5 | 0.37 | 0.17 | 2.2 | 950 | 0 | 80 | 52 | 35% |

H2S MEASURED DOWNSTREAM APPROX 1000 FT FROM CHEMICAL INJECTION POINT. SEWAGE FLOW IS 6-7 FT/SEC AND CONTAINS 3-4 mg/L DISSOLVED SULFIDE.

FIG. 3

IN SITU GAS SCRUBBING METHOD AND SYSTEM FOR ODOR AND CORROSION CONTROL IN WASTEWATER COLLECTION SYSTEMS

TECHNICAL FIELD

The present invention pertains to a method and system for in situ spray fogging a mixture of hydrogen peroxide and alkali to reduce hydrogen sulfide concentrations in enclosed spaces, including gravity sewers and other structures in sewage collection systems.

BACKGROUND ART

Control of gaseous hydrogen sulfide and other gaseous sulfur compounds in sewage treatment systems, including gravity sewers, sewage pumping stations and other structures in sewage collection systems and treatment plants has been a long-standing problem. Relatively small diameter branch lines as well as large diameter trunk sewer lines and interceptors entering sewage treatment plants may extend substantial distances before a system collection and treatment station is available for treatment of foul air by conventional gas scrubber equipment and systems. Over such substantial distances odorous and toxic gases, such as hydrogen sulfide, may escape into the environment in proximity to a sewage system which can result in unhealthy, dangerous and clearly unpleasant circumstances for persons in the vicinity of such a system.

Moreover, the presence of toxic gases, such as hydrogen sulfide, in the vapor spaces of sewage conduits and in slimes which tend to accumulate on the conduit walls results in the formation of acids which contribute to significant corrosion of the conduits. Accordingly merely treating the liquid influent in a conduit does not result in treatment of acid substances which accumulate and are retained on the conduit walls and can cause significant corrosive action.

Furthermore, the expansion of municipal sewage collection and treatment systems as a consequence of residential and commercial development in a municipality or a change in the composition of sewage usually requires expansion of a central treatment facility including the addition of foul air treatment equipment such as conventional mist or packed-tower-type scrubbers. These devices are particularly capital intensive and require substantial maintenance effort and expense.

Still further, sewage collection and treatment systems which are subject to increased capacity requirements or systems which may over a period of time require handling of various concentrations of material which produce the noxious gases referenced hereinabove could benefit from localized control of foul air in the collection system and associated structures. The addition of air handling equipment and conventional scrubbers at such locations may be impractical and, of course, can require substantial expense. However, the present invention provides a method and system which overcomes, substantially, the aforementioned problems by utilizing the sewage handling structures themselves as foul air treatment or gas scrubber structures which provides significant advantages as will be appreciated by those skilled in the art.

DISCLOSURE OF THE INVENTION

The present invention provides a method of localized control of odor and corrosion in gravity sewers, sewage pumping stations and other structures in sewage collection systems and treatment plants by utilizing sewer conduits, plenums and similar structures for treatment of air-borne contaminants, such as hydrogen sulfide and other noxious and toxic gases, flowing through a sewage system and the like.

In accordance with one important aspect of the invention, a method is provided for injecting a dilute oxidizing liquid spray, mist or fog into the air space above flowing sewage in sewage structures, such as gravity sewers and the like, upstream of pumping stations or treatment plant headworks. The method contemplates providing a treatment injection point upstream of the area or structure where odor and/or corrosion control are required so that sufficient time is allowed for oxidation and/or adsorption of air-borne contaminants, including hydrogen sulfide and other reduced sulfur compounds.

In accordance with another aspect of the invention, a method of air-borne odor and corrosion control is provided in situ in sewer systems by injecting an alkali and peroxide solution through one or more atomizing or spray nozzles into a sewage conduit above the flowing influent and in quantities in proportion to the expected levels of toxic gases, such as hydrogen sulfide. The solution may be premixed and injected through a nozzle array into the foul air in the sewage system or the alkali and peroxide treatment components may be injected separately but in the vicinity of each other into the conduit. The method contemplates that the mist or fog is drawn along the sewage conduit by the flowing sewage and vapors in the vapor space of the conduit. Such vapor flow may be assisted by mechanical pumps or fans to draw the treated air and vapor mixture through a pump station or existing foul air scrubbing or treatment apparatus.

In accordance with still another aspect of the present invention, an improved method of corrosion control in sewage handling and treatment system is provided by injecting an oxidizing agent into sewage conduits at selected locations to oxidize air-borne hydrogen sulfide and other reduced sulfur compounds to prevent traversal of corrosive compounds through the entire sewage system and any treatment facilities connected thereto. The method contemplates the injection of a mixture of an oxidizing agent, such as hydrogen peroxide, and an alkali, such as sodium hydroxide. The use of an alkali is beneficial to assist the adsorption of the hydrogen sulfide into the spray/mist or fog, to accelerate the oxidation reaction and to neutralize the production of sulfuric acid from the reaction.

In accordance with yet another aspect of the invention, a method for odor control in sewage systems is provided wherein enclosed spaces in gravity sewers and similar structures are subject to the injection of a spray, mist or fog of diluted alkali, such as sodium hydroxide, at a point upstream of where odor control is required to temporarily neutralized the adverse effects of odorous substances, such as hydrogen sulfide, and in order to provide sufficient time for other injection agents to react with such contaminants in the enclosed spaces so as to permanently neutralize the adverse effects.

The present invention still further provides a system for injecting a spray or mist of an oxidizing agent and an adsorbing and ionizing agent for oxidizing toxic gases, such as hydrogen sulfide, and other sulfur compounds present in the air spaces of sewage handling and treatment systems and similar structure, which system may be placed permanently or temporarily at selected locations in sewage conduits, for example, upstream of a source of production of hydrogen sulfide and similar toxic gases. The system is adapted to mix and inject a dilute solution of hydrogen peroxide and sodium hydroxide as oxidizing and adsorption agents directly into a sewer pipe vapor space or plenum of a sewage handling structure to create intimate contact between the chemical spray or mist and the toxic vapors and contaminants in the vapor space. The system is capable of injecting a spray, mist or fog depending on the pressure and flow rates of the injected fluids.

In accordance with yet another aspect of the present invention, a system for injecting a spray, mist or fog of an oxidizing agent and an adsorption and ionizing agent into the air space of sewage handling and treatment structures is provided wherein a dilution water stream may be added to the oxidizing and alkaline adsorption agents prior to passing these agents through one or more atomizing or spray nozzles. Conversely, the oxidizing and adsorption agents may be added to a tank of dilution water from which a final solution is pumped through the spray nozzles. The system may be operated continuously when the concentration of the toxic contaminants, such as hydrogen sulfide, is great enough to warrant abatement thereof.

The system and method of the invention also provides the advantage that any of the adsorption and oxidizing agents, with or without dilution water, which are unreacted with airborne contaminants may be deposited on sewage conduit walls to neutralize corrosive substances deposited thereon and/or the agents merely fall into flowing liquid sewage in a sewage conduit or the bottom of a dry plenum or other structure. In this way unreacted agents will react with sulfides in the sewage influent resulting in further reduction of concentrations of toxic substances, such as hydrogen sulfide, and the adverse effects of same. Moreover, any unreacted oxidizing agent may provide dissolved oxygen to the sewage influent stream.

Those skilled in the art will further appreciate the above-mentioned features and advantages of the invention together with other superior aspects thereof upon reading the detailed description which follows in conjunction with the drawing.

BRIEF DESCRIPTION OF THE DRAWINGS

FIGS. 2 and 3 are tables indicating the reduction in concentration of hydrogen sulfide in a dry plenum and a sewage trunk line, respectively, in accordance with the method and system of the present invention.

BEST MODES FOR CARRYING OUT THE INVENTION

Figure 1:
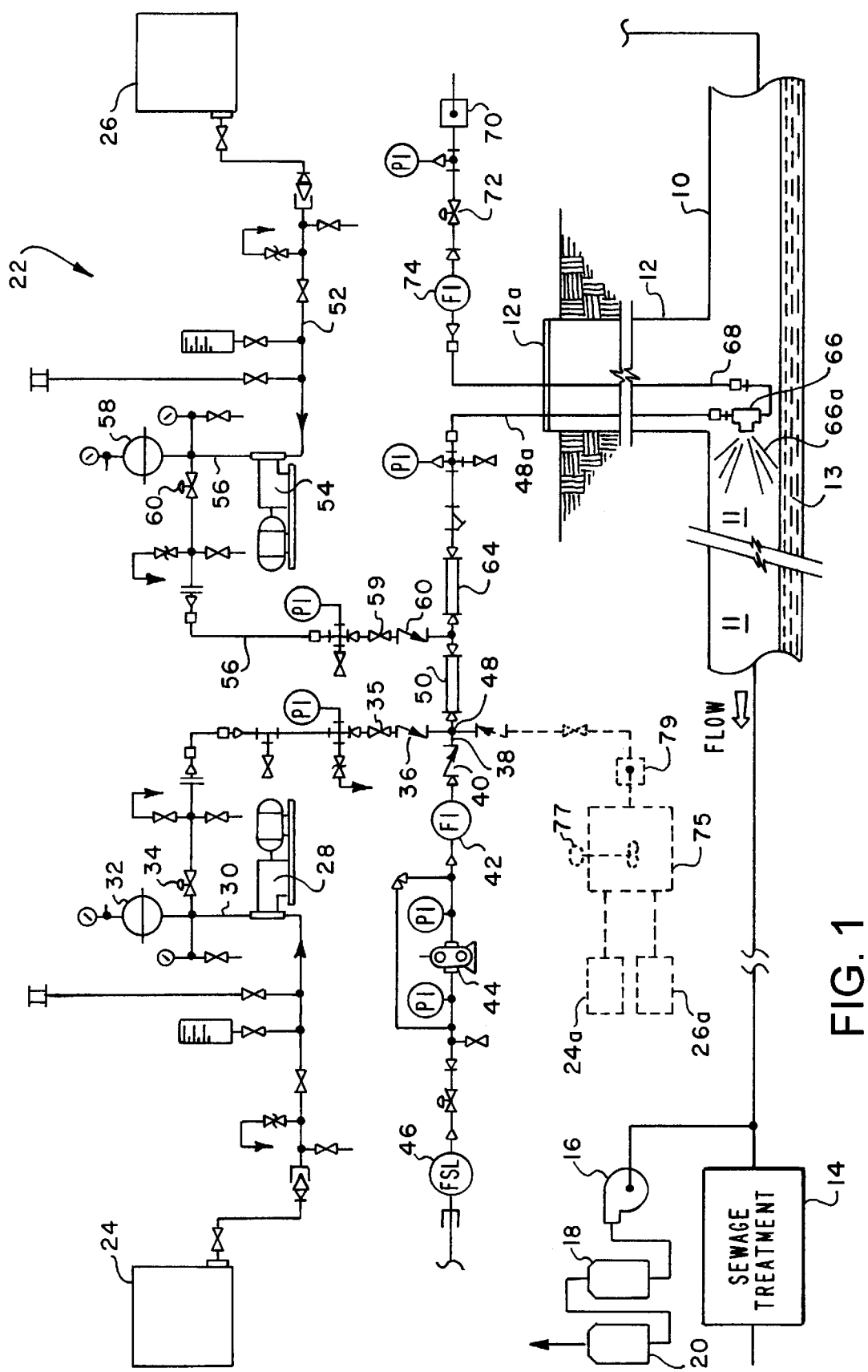
FIG. 1 is a schematic diagram of an embodiment of a system in accordance with the invention for injecting an alkaline and peroxide mist into a vapor space of a sewage handling system to reduce odorous and corrosive contaminant concentrations therein.

In the description which follows, like elements are marked throughout the specification and drawing with the same reference numerals, respectively. The drawings are not to scale and at least certain conventional elements are shown in schematic form using conventional symbols for same.

The cost of abating hydrogen sulfide and other toxic and offensive contaminants in municipal sewage or wastewater handling and treatment facilities is significant. Conventional methods for abating air-borne hydrogen sulfide and other corrosive and odorous contaminants in the air spaces of sewage or wastewater handling and treatment facilities requires frequent maintenance, frequent replacement of the treatment equipment and replacement or regeneration of compositions used therein. For example, conventional treatment systems include batteries of packed-tower scrubbers as well as carbon-filled dual bed adsorption towers, for example. Air handling equipment connected to the sewage trunk lines conveys the contaminated air to this treatment equipment for abatement of the offensive and corrosive air-borne contaminants. The exposure of all of this equipment to contaminants, such as hydrogen sulfide, for example, is a significant operations and cost problem.

The initial capital cost, moderate to high maintenance cost, including periodic cleaning and/or replacement of packing, replacement of or regeneration of carbon beds and chemical consumption are significant disadvantages to this type of equipment. Moreover, the placement of this equipment in a sewer system does not prevent corrosion of other equipment in the sewer lines or other parts of the system structures. New or relatively small capacity sewage or foul air generating systems may not include this type of air handling equipment and the initial cost and modification of the system to accommodate same is noteworthy.

Moreover, in existing sewage handling and treatment systems increased concentrations of air-borne contaminants, including hydrogen sulfide, can result from temporary or permanent increased sewage loadings at various points in the system at various times, including at incoming lines to lift stations, pump stations and treatment plants. These increased loadings may require additional conventional treatment equipment of the type mentioned above. However, with the present invention, the cost of equipment for treating foul, contaminated air in sewage handling and treatment systems and related systems can be substantially less than implementing treatment using conventional equipment and methods. It has also been discovered that, with the method and system of the present invention, the time available for reaction of air-borne contaminants with oxidizing and adsorption agents is significantly increased, the system occupies a significantly smaller space than conventional equipment and corrosion of the sewage or wastewater handling conduit network, associated structures and equipment is reduced.

The method of the invention contemplates providing compositions for oxidizing and the adsorption and ionization of air-borne hydrogen sulfide vapors to reduce concentrations of these vapors in any vapor space that is delimited by an enclosure, particularly, municipal and industrial sewer conduits, dry plenums and stacks. While the invention contemplates reducing the expected concentrations of hydrogen sulfide, other gaseous compounds including mercaptans, sulfur dioxide, amines and aldehydes can also be treated by the method of the invention. Sodium hydroxide may be used to adsorb hydrogen sulfide vapors from a vapor space and ionize the hydrogen sulfide to sulfide anion. This action alone provides at least temporary abatement of the odorous substance. The hydrogen peroxide will then oxidize the sulfide anion to sulfate. One or more atomizing spray nozzles or devices are placed in the vapor space of a sewer trunk line or similar conduit in order to cover the cross-sectional area of the conduit pipe or plenum vapor space sufficiently to provide intimate contact between the spray pattern and the hydrogen sulfide vapors flowing through the vapor space. The walls of the plenum or conduit, of course, prevent the hydrogen sulfide vapors from spreading beyond the reach of the spray pattern.

The concentrations of the preferred chemicals for use in the method of the invention contemplate up to 52% by weight of hydrogen peroxide and up to 50% by weight of sodium hydroxide. Preferred concentrations of hydrogen peroxide are 35% to 50% and between 20% and 30% concentration for sodium hydroxide. Prior to injection through a spray, mist or fog nozzle or "head," the hydrogen peroxide is preferably diluted to between 1% and 5% by weight and the sodium hydroxide is preferably diluted to between 1% to 3% by weight, both with water. Dilution may be made on-line using the system illustrated in FIG. 1 and to be described in further detail hereinbelow. In such instances conventional tap water may be used since the diluted hydrogen peroxide will be used essentially immediately after mixing resulting in negligible decomposition of the oxidizing agent. However, if the dilute alkaline-hydrogen peroxide mixture is to be pre-mixed and stored for several hours or days before injection into the contaminated vapor space, deionized water should be used to minimize decomposition. Some decomposition will occur however due to the presence of alkali.

A minimum mole-ratio of sodium hydroxide to hydrogen peroxide of 2:1 and a minimum mole-ratio of hydrogen peroxide to hydrogen sulfide of 4:1 should be maintained for a stoichiometric reaction. A wide-range of mole-ratios for each free agent may be used, however. The use of less than a 4:1 mole-ratio of hydrogen peroxide to hydrogen sulfide will result in less than stoichiometric levels of hydrogen sulfide being destroyed but the level of destruction achieved may be adequate. Greater than a 4:1 mole-ratio of hydrogen peroxide to hydrogen sulfide may be necessary in environments where, for example, hydrogen peroxide decomposition may be excessive such as in sewers and plenums where there are other reactive vapors in addition to hydrogen sulfide. Greater than a 2:1 mole-ratio of sodium hydroxide to hydrogen sulfide may also be necessary wherein, for example, acid vapors may coexist with the hydrogen sulfide. Moreover, the normally significant concentration of carbon dioxide in sewer air also tends to increase the consumption of sodium hydroxide in this application.

The choice of concentrations of the reactive agents depend on the optimum operating range of the spray, mist or fog nozzles as well as the number of nozzles. The fluid supply pressure of the diluted hydrogen peroxide and sodium hydroxide at the spray nozzles will also influence the final concentration to be used. Atomizing air flow rates of about 7.0 standard cubic feet per minute (scfm) to 45.0 scfm and dilution water flow rates of 1.4 gallons per minute to 1.8 gallons per minute have been used at injection pressures of 60 PSIG to 69 PSIG of water with desirable results. Injection of sodium hydroxide alone will result in the adsorption of hydrogen sulfide to reduce the concentration of the hydrogen sulfide in the vapor space. The sulfide will still be present in the condensed alkaline solution from the system and a reduction of pH below 9.0 will release the hydrogen sulfide back into the atmosphere if only the adsorption and ionizing agent alone is used. However, when hydrogen peroxide is used in combination with the sodium hydroxide, the perhydroxyl ion provides for the hydrogen sulfide to be destroyed through oxidation to sulfate preventing any chemical reversion back to hydrogen sulfide. The hydrogen peroxide may be injected directly into influent flowing through the conduit or structure at a point just downstream of the point of spray injection into the vapor space.

After the hydrogen sulfide is reacted with the above-mentioned agents an aqueous condensate containing sodium sulfate, unreacted sodium hydroxide, unreacted hydrogen peroxide and water will fall into the flowing sewage or wastewater or to the bottom of a dry plenum or other structure. Any hydrogen peroxide remaining will harmlessly decompose over time and, where contaminated water or sewage is present, the unreacted hydrogen peroxide will react with sulfides in the sewage fluid resulting in even greater reduction of hydrogen sulfide concentrations and provide additional dissolved oxygen in the sewage. Any air-borne droplets of spray, mist or fog of the reacting chemicals reaching the downstream end of a sewage system may exit the system through vent stacks or through foul air handling or treatment equipment. Moreover, any unreacted agents in the spray, mist or fog will also tend to coat the surfaces of the sewage conduit and react with acid slime and the like coating the walls of the conduit to neutralize same and reduce corrosion of the conduit structure.

Referring now to FIG. 1, there is illustrated a system for injecting a water-diluted mixture of reactive agents, such as hydrogen peroxide and sodium hydroxide, into a sanitary sewer trunk line or conduit 10. Conventional sewer systems have spaced-apart access conduit branches or manways, such as the manway 12 illustrated. FIG. 1 also illustrates some basic components of a sewage system including a downstream treatment facility 14 and a foul air handling facility including a suction fan 16 and a battery of series connected scrubbers 18 and 20. The sewer system illustrated and described is exemplary and the system and method of the invention may be carried out in a wide variety of sewage handling and treatment systems as well as other structures having a contaminated vapor space requiring treatment in accordance with the invention. The system illustrated in FIG. 1 is preferably installed in a sewer conduit, such as the conduit 10, a sufficient distance upstream from the end of the system, including the treatment facility 14 and the foul air handling facilities 16, 18 and 20, as to allow sufficient reaction time to reduce the volatile and toxic substances in the vapor space 11 not occupied by liquid sewage 13.

Referring further to FIG. 1, the exemplary system illustrated schematically is well suited to testing the ability to reduce concentrations of hydrogen sulfide and similar contaminants as well as maintaining reduced concentrations long term. The system is generally designated by the numeral 22. Certain conventional components such as certain shut-off valves, check valves and take-off valves, pressure gauges, vents, connectors and other devices used in a test system are illustrated in FIG. 1 but may not be described in detail herein in the interest of clarity and conciseness. Essential elements for any system in accordance with the invention are described below and will be understandable to those skilled in the art from the diagram of FIG. 1. The system 22 may be essentially self-contained including a source of power, not shown, and either skid or vehicle mounted for temporary placement at a location requiring reduction of odorous and corrosive contaminants such as hydrogen sulfide in a sewage system. Alternatively, the system 22 may be permanently installed at a desired site and operated, as needed, to reduce concentrations of hydrogen sulfide in the conduit vapor space 11, for example.

The system 22 includes conventional storage vessels 24 and 26 for storing quantities of hydrogen peroxide and sodium hydroxide, respectively, and in the concentrations indicated above, respectively. Although a preferred adsorption and ionizing agent is sodium hydroxide other base chemicals such as potassium hydroxide, sodium carbonate and ammonium hydroxide may be used, for example. The storage vessel 24 is connected to a suitable motor-driven metering pump 28, such as a Pulsafeeder model 7120, the discharge conduit 30 of which is connected to a suitable pulsation dampener 32, such as a Pulsatrol model 78, and an in-line back pressure valve 34. The discharge conduit 30 is also connected to a suitable shutoff valve 35, check valve 36 and to a water injection conduit 38 having a check valve 40 and flow meter 42 interposed therein. Water injection conduit 40 is in communication with a motor-driven pump 44, such as a Liquiflo model 35RS, and a flow limiting device 46 connected to a source of water, not shown. Conduits 30 and 38 become a common conduit 48 in which a suitable in-line fluid mixing device 50 is interposed. Mixing device 50 may be a Cole-Parmer static mixer, for example.

Referring further to FIG. 1, the storage vessel 26 is also connected by way of a conduit 52 to the inlet of a motor-driven metering pump 54, substantially like the pump 28 whose discharge conduit 56 is connected to a pulsation dampener 58 and a back pressure control valve 60 in the same manner as the pump 28 and using the same type of devices. Discharge conduit 56 is connected by way of a shutoff valve 59 and a check valve 60 to the conduit 48 downstream of the mixer 50, as indicated. A second, in-line mixer 64, similar to the mixer 50, is interposed in conduit 48 for mixing the water diluted hydrogen peroxide with the sodium hydroxide thoroughly before conducting the mixed solution through a suitable substantially rigid conduit 48a extending through a conventional or modified manway cover 12a into the manway 12. The conduit 48a is connected to one or more atomizing nozzles or heads 66, one shown, disposed in the vapor space 11. The nozzle(s) 66 may be Lechler model 156.103.16.03 air mist pressure spray nozzles, for example.

Depending on the size of the sewage conduit undergoing treatment, one or more nozzles 66 may be arranged in parallel in a suitable array to provide a spray pattern, such as the spray pattern 66a, which will cover the entire cross-sectional area of the vapor space 11 to provide intimate contact between the injected solution and the contaminated air flowing through the vapor space 11. The atomizing nozzle 66 is connected via a conduit 68 extending within the manway 12 to a source of pressure air comprising a compressor 70. A suitable pressure-regulator valve 72 is interposed in conduit 68 downstream of compressor 70 and an in-line flow meter 74 may also be provided for test and monitoring purposes as indicated.

The system 22 provides for pre-mixing the adsorption and ionizing agent with the oxidizing agent which, in fact, results in a conversion of at least some of the mixture into monosodium peroxide which becomes the oxidizing agent. The two agents contemplated for use in accordance with the invention may also be injected separately through separate spray nozzles in the vapor space 11, which nozzles may be placed closely adjacent each other in a suitable pattern to provide thorough intimate contact of all of the air flowing through the conduit 10 with the reactive chemicals. Suitable controls for controlling the operation of the pumps 28, 44 and 54 and compressor 70 are not shown but are believed to be within the purview of one skilled in the art.

The system 22 may be modified as shown by the dashed lines in FIG. 1 to provide a common storage vessel 75 connected to component storage vessels 24a and 26a and providing for storage in vessel 75 of a mixture of hydrogen peroxide, sodium hydroxide and dilution water. Such a vessel should be equipped with a mixer 77 to insure the chemicals are well-mixed with the dilution water and the diluted solution may then be pumped through a single metering pump 79 to the conduit 48, 48a. The static in-line mixers 50 and/or 64 may remain interposed in line 48 upstream of injection spray nozzle or nozzles 66. An atomizing nozzle, such as the nozzle 66, utilizing a separate source of propellant, such as compressed air, is advantageous. However, the mixture may be injected into the vapor space 11 through a suitable spray nozzle which does not require an atomizing or misting propellant.

As noted from FIG. 1, it is particularly advantageous to install the system 22 in the conduit 10 a significant distance upstream of the flow-inducing fan 16 to assure thorough mixing of the injected chemical solution in the vapor space 11 and to allow for sufficient chemical reaction time in the flow of contaminated air through the space 11 before such reaches the treatment facility 14 and the air handling and treatment system 16, 18 and 20, if used. In all events, even with naturally induced flow of air or vapor through the conduit 10, the location of the system 22 in the conduit should be such as to maximize reaction time between the agents, such as hydrogen peroxide and sodium hydroxide, and a major contaminant, such as hydrogen sulfide.

EXAMPLE 1

Using a system substantially like the system 22 except with two parallel mounted atomizing nozzles 66 connected to the conduits 48a and 68, a dilute mixture of hydrogen peroxide and sodium hydroxide was injected into a dry plenum carrying hydrogen sulfide vapors from a municipal sewer system. The rectangular plenum was approximately 4.0 feet wide by 7.0 feet deep and a series of flow inducing fans was located approximately 1,000 feet downstream from the point of chemical injection to induce flow of vapors through the plenum. Hydrogen sulfide concentration measurements were made in the vapor flowstream before and during each treatment using an Industrial Scientific hydrogen sulfide meter located at a conventional scrubber inlet port approximately 1,000 feet downstream of the chemical injection point. The conditions and results of the process are summarized in FIG. 2. The average hydrogen sulfide concentration at the measurement point and indicated in the left column of FIG. 2 is shown before and during chemical injection. Test runs A, B and C were triplicate runs using a 2.2:1 mole-ratio of hydrogen peroxide to sodium hydroxide at flow rates of 10.0 gallons per hour (gph) for 50% by weight hydrogen peroxide and 25% by weight sodium hydroxide. The chemical streams were diluted with 96.0 gph of water before being combined and sent through the spray nozzles. Hydrogen sulfide reductions ranged from 24% to 36% over a pretreatment concentration of hydrogen sulfide in the range of 62 ppm to 94 ppm. Test run D indicates a reduced flow rate of hydrogen peroxide and sodium hydroxide to 5.0 gph each resulting in a 32% reduction in hydrogen sulfide concentration placing this test in the same range as a reduction in concentration for tests at double the flow rate of reactive agents. However, as indicated for test run E, reducing the hydrogen peroxide and sodium hydroxide flow rates further to 2.5 gph each, resulted in a hydrogen sulfide abatement of only 16% reduction, indicating that concentrations being treated at injection rates of greater than 2.5 gph up to about 5.0 gph were optimum.

Test run F shows that the injection of hydrogen peroxide alone at a rate of 10.0 gph resulted in only about a 6% hydrogen sulfide abatement, indicating the importance of having alkaline conditions present when using hydrogen peroxide. Conversely, using sodium hydroxide alone at a rate of 10.0 gph resulted in a 31% hydrogen sulfide abatement as indicated in FIG. 2 for test run G. However, as indicated previously, using the adsorption and ionizing agent, such as sodium hydroxide, alone might result in the release of hydrogen sulfide back into the atmosphere before the flowstream reached downstream handling equipment, if present.

EXAMPLE 2

Referring now to FIG. 3, there is indicated the results of tests conducted on a 108 inch diameter gravity sewer conduit through which an average flow rate of sewage influent was 150 million gallons per day (mgd) at a velocity of 6.0 to 7.0 feet per second (ft./sec.). Dissolved hydrogen sulfide concentration was 3.0 to 4.0 milligrams per liter (mg/l). The vapor space within the sewer conduit ranged from 20% to 40%. A three-nozzle spray unit was used for the test, the results of which are shown in FIG. 3, with in-line water dilution of hydrogen peroxide and sodium hydroxide using a system substantially like the system of FIG. 1 but with the added spray nozzles. As shown in FIG. 3, four baseline runs 1A, 1B, 1C and 1D showed hydrogen sulfide vapor concentrations of 70–175 ppm without treatment. Injecting water alone through the spray system reduced the hydrogen sulfide concentration by only 8% (test run 2A). Injecting sodium hydroxide alone at 5.0 gph and a concentration of 55 ppm of hydrogen sulfide resulted in a 53% reduction as indicated by test run 3A. Still further, injecting sodium hydroxide at a rate of 10.0 gph with a baseline concentration of hydrogen sulfide of 175 ppm resulted in a 54% reduction in atmospheric hydrogen sulfide (test run 4A).

As might be expected from the foregoing test results using hydrogen peroxide alone at a rate of 5.0 gph with a 70 ppm hydrogen sulfide baseline concentration resulted in only a 14% reduction of hydrogen sulfide in the vapor space as indicated by test run 5A. However, flow rates of 5.0 gph for both hydrogen peroxide and sodium hydroxide (2.2:1 mole ratio and near the stoichiometric mole ratio of 2:1) with a 155–170 ppm baseline concentration of hydrogen sulfide resulted in reductions of 57% to 58% as indicated by test runs 6A and 6B. Test runs 7A and 7B indicate that a 5.0 gph flow rate of both hydrogen peroxide and sodium hydroxide and only a 45–70 ppm baseline concentration of hydrogen sulfide resulted in a 66% to 67% abatement rate.

As might be expected, considering the foregoing reported in connection with the tests of EXAMPLE 1 and FIG. 2, doubling the flow rates of the reactive chemicals did not increase the level of abatement of hydrogen sulfide, as indicated by the 66% abatement resulting from the test run 8A. Adding hydrogen peroxide at 5.0 gph and sodium hydroxide at 10.0 gph with a baseline concentration of hydrogen sulfide in the vapor space of 160–170 ppm also did not improve the removal rate of hydrogen sulfide over the test runs of the conditions indicated for runs 7A and 7B. Moreover, test runs 9A and 9B indicate that the deficiency of hydrogen peroxide may have resulted in some unreacted sulfide remaining in the alkaline condensate.

Conversely, doubling the hydrogen peroxide flow to 10.0 gph while keeping the sodium hydroxide flow at 5.0 gph with a 170 ppm baseline concentration resulted also in a 57% reduction in hydrogen sulfide vapor as indicated by test run 10A.

Finally, reducing the hydrogen peroxide and sodium hydroxide flows to 2.5 gph with a baseline concentration of hydrogen peroxide of 80 ppm resulted in only a 35% decrease in the hydrogen sulfide concentration as indicated by test run 11A. During the conduction of the tests described above and the results of which are shown in FIG. 3 it is likely that additional hydrogen sulfide was being released into the sewage conduit vapor space due to the rapid flow rate and the usual pH of about 6.5 to 7.5 found in municipal sewage. Hydrogen sulfide will be released in waters that are below a pH of 9 with more rapid release as the pH is lowered.

It is contemplated in accordance with the invention that the system 22 may be used in treating vapor spaces in plenums and sewage conduits wherein the concentration of odorous contaminants, including hydrogen sulfide, ranges from about 1 ppm to 5,000 ppm. Typically, the injection process will be commenced when a measured concentration in the range indicated above is obtained, or from other conditions observed it may be estimated that a concentration within such range is present. Although a preferred method and system in accordance with the invention have been described in detail herein those skilled in the art will recognize that various substitutions and modifications may be carried out without departing from the scope and spirit of the invention as recited in the appended claims.

We claim:

1. A process for reducing odorous contaminant concentration comprising hydrogen sulfide in a vapor space of a sewage conduit through which a flow of vapor including said hydrogen sulfide is being induced and through which liquid sewage is flowing toward a sewage treatment plant, comprising the steps of:

providing a system including at least one spray nozzle connected to conduit means for conducting an alkaline-peroxide reagent comprising a first solution of base selected from a group consisting of sodium hydroxide, potassium hydroxide, ammonium hydroxide and sodium carbonate and a second solution comprising hydrogen peroxide for injection into said vapor space;

placing said spray nozzle in said vapor space above a surface of said liquid flowing through said sewage conduit at a point upstream of a point of inducing said flow of vapor through said vapor space such as to provide a spray pattern extending substantially across the cross sectional area of said vapor space above said surface of said liquid; and injecting said first solution and said second solution into said vapor space through said spray nozzle in a fine spray to provide intimate contact between said solutions and said odorous contaminant to oxidize said odorous contaminant and to contact a wall of said sewage conduit delimiting said vapor space to reduce corrosion thereof.

2. The process set forth in claim 1 wherein:

said second solution is provided as a solution of hydrogen peroxide in a minimum mole ratio to hydrogen sulfide of 4:1 and said first solution comprising said base is provided in a minimum mole ratio to hydrogen peroxide of 2:1.

3. The process set forth in claim 2 including the step of:

providing said second solution as a diluted solution of hydrogen peroxide in a concentration of one percent to five percent by weight.

4. The process set forth in claim 2 including the step of:

providing said first solution as a diluted solution in a concentration of said base of one percent to three percent by weight.

5. The process set forth in claim 1 including the step of:

providing said system comprising:

a source of said base;

a metering pump operably connected to said source of said base and to said conduit means for conducting a metered flow of said solution of said base to said spray nozzle;

a source of said hydrogen peroxide;

a metering pump operably connected to said source of hydrogen peroxide and to said conduit means for conducting a metered flow of said solution of hydrogen peroxide to said spray nozzle;

a metering pump operably connected to a source of water and to said conduit means for conducting dilution water to mix with said base and said hydrogen peroxide prior to injection through said spray nozzle into said vapor space;

a mixer for mixing water with said hydrogen peroxide and said base to provide a dilute mixed solution of said alkaline-peroxide reagent for injection through said conduit means and said spray nozzle into said vapor space; and a source of pressure air connected to said spray nozzle for atomizing said solution of alkaline-peroxide reagent to form said spray pattern.

6. The process set forth in claim 5 including the step of:

providing said mixer comprising a first mixer for receiving a solution of water and one of said base and said hydrogen peroxide and a second mixer for receiving a mixed solution of said water and said one of said base and hydrogen peroxide and for mixing the other of said base and said hydrogen peroxide with said mixed solution prior to injection of said alkaline-peroxide reagent into said vapor space.

7. The process set forth in claim 5 including the step of:

providing said system with shutoff valve means interposed in respective conduits between said metering pumps and said sources of said base and said hydrogen peroxide, respectively, for controlling the flow of said base and said hydrogen peroxide through said conduit means and said spray nozzle.

8. A process for reducing odorous contaminant concentration comprising at least one of hydrogen sulfide, mercaptans, sulfur dioxide, amines and aldehydes in a vapor space of a sewage conduit through which a flow of vapor including said odorous contaminant is being induced and through which liquid sewage is flowing toward a sewage treatment plant, comprising the steps of:

providing a system including at least one spray nozzle connected to a conduit for conducting an alkaline-peroxide reagent therethrough and adapted to be inserted into said vapor space of said sewage conduit, said system further comprising a source of a base in solution and selected from a group consisting of sodium hydroxide, potassium hydroxide, ammonium hydroxide and sodium carbonate, a metering pump operably connected to said source of said base and to said conduit for conducting a metered flow of said solution of said base to said spray nozzle, a source of said hydrogen peroxide, a metering pump operably connected to said source of hydrogen peroxide and to said conduit for conducting a metered flow of solution of hydrogen peroxide to said spray nozzle, a metering pump operably connected to a source of water and to said conduit for conducting dilution water to mix with said base and said hydrogen peroxide prior to injection through said spray nozzle into said vapor space, a mixer for mixing water with said hydrogen peroxide and said base to provide a dilute mixed solution of said alkaline-peroxide reagent for injection through said conduit and said spray nozzle into said vapor space, and a source of pressure air connected to said spray nozzle for atomizing said solution of alkaline-peroxide reagent to form a spray pattern extending substantially across the cross sectional area of said vapor space above a surface of said liquid in said sewage conduit;

placing said spray nozzle in said vapor space above said surface of said liquid in said sewage conduit at a point such that said spray pattern extends substantially across the cross sectional area of said vapor space above said surface of said liquid to provide intimate contact between said solutions and said odorous contaminant and to contact a wall of said sewage conduit delimiting said vapor space to reduce corrosion thereof; and injecting said solutions into said vapor space through said spray nozzle in a fine spray to provide said intimate contact between said solutions and said odorous contaminant to oxidize said odorous contaminant and to contact said wall to reduce corrosion thereof.

9. A system for injecting an alkaline-peroxide reagent into a vapor space of a sewage handling conduit contaminated with hydrogen sulfide at a point upstream of a sewage treatment plant, said system including:

a substantially rigid fluid conducting conduit for insertion through a manway into said sewage handling conduit and supporting at least one spray nozzle for disposition in said vapor space of said sewage handling conduit, said conduit and said nozzle being configured for injecting a spray of said alkaline-peroxide reagent into said vapor space in a spray pattern extending substantially across the cross-section of said vapor space and to contact a wall of said sewage handling conduit defining said vapor space for mixing said alkaline-peroxide reagent with hydrogen sulfide contaminated vapor flowing through said vapor space and for reducing corrosion of said wall;

a source of a base selected from a group consisting of sodium hydroxide, potassium hydroxide, ammonium hydroxide and sodium carbonate;

a metering pump operably connected to said source of said base and said rigid conduit for conducting a metered flow of a solution of said base to said nozzle;

a source of hydrogen peroxide;

a metering pump operably connected to said source of hydrogen peroxide and to said rigid conduit for conducting a metered flow of a solution of hydrogen peroxide to said nozzle;

a metering pump operably connected to a source of water and to said rigid conduit for conducting dilution water to mix with said base and said hydrogen peroxide prior to injection through said nozzle into said vapor space; and an arrangement of fluid mixers for mixing said water with said hydrogen peroxide and said base to provide a dilute mixed solution of alkaline-peroxide reagent for injection into said vapor space through said nozzle.

10. The system set forth in claim 9, including:

a source of pressure air connected to said nozzle for atomizing said solution of alkaline-peroxide reagent to form said spray pattern in said vapor space.

11. The system set forth in claim 9, wherein:

said arrangement of mixers comprises a first mixer for receiving a solution of water and one of said base and hydrogen peroxide and a second mixer for receiving a mixed solution of water and said one of said base and hydrogen peroxide and for mixing the other of said base and hydrogen peroxide with said mixed solution prior to injection of said alkaline-peroxide reagent into said vapor space.

12. The system set forth in claim 9, including:

shut-off valves interposed in respective conduits between said metering pumps and said sources of said base and said hydrogen peroxide, respectively, for controlling the flow of said base and said hydrogen peroxide through said system.

* * * * *